United States Patent [19]
Shi et al.

[11] Patent Number: 6,096,524
[45] Date of Patent: Aug. 1, 2000

[54] CHEMICALLY DERIVED MALTODEXTRINS

[75] Inventors: Yong-Cheng Shi, Somerville; James L. Eden, Millstone; James J. Kasica, Whitehouse St., all of N.J.

[73] Assignee: National Starch and Chemical Investment Holding Corporation, Wilmington, Del.

[21] Appl. No.: 09/078,766

[22] Filed: May 14, 1998

Related U.S. Application Data

[62] Division of application No. 08/643,644, May 6, 1996, Pat. No. 5,795,397.

[51] Int. Cl.⁷ .............................. C12P 19/14; C08B 31/04
[52] U.S. Cl. .................................. 435/99; 435/95; 435/96; 435/135; 536/110; 536/108; 536/107; 536/102; 536/124
[58] Field of Search .................... 435/99, 95, 96, 435/135; 536/110, 108, 107, 124, 102

[56] References Cited

U.S. PATENT DOCUMENTS

| | | | |
|---|---|---|---|
| 2,609,326 | 9/1952 | Pigman et al. | 195/31 |
| 2,808,381 | 10/1957 | Stone | 260/17.4 |
| 3,505,110 | 4/1970 | Kesler et al. | 127/29 |
| 3,560,343 | 2/1971 | Armbruster et al. | 127/29 |
| 3,639,389 | 2/1972 | Hull | 260/233.3 |
| 3,644,126 | 2/1972 | Bodnar | 99/142 |
| 3,663,369 | 5/1972 | Morehouse et al. | 195/31 |
| 3,849,194 | 11/1974 | Armbruster et al. | 127/29 |
| 3,853,706 | 12/1974 | Armbruster | 195/31 R |
| 3,922,196 | 11/1975 | Leach | 435/99 |
| 3,922,197 | 11/1975 | Leach | 435/99 |
| 3,922,199 | 11/1975 | Hebeda | 435/99 |
| 3,974,034 | 8/1976 | Horn et al. | 195/31 R |
| 4,014,743 | 3/1977 | Black | 195/31 R |
| 4,035,235 | 7/1977 | Richards et al. | 195/31 |
| 4,052,226 | 10/1977 | Verbanac | 127/29 |
| 4,241,183 | 12/1980 | Witt | 435/95 |
| 4,316,956 | 2/1982 | Lutzen | 435/96 |
| 4,447,532 | 5/1984 | Coker et al. | 435/99 |
| 4,643,894 | 2/1987 | Porter et al. | 424/35 |
| 4,725,441 | 2/1988 | Porter et al. | 424/479 |
| 4,828,841 | 5/1989 | Porter et al. | 424/479 |
| 4,921,795 | 5/1990 | Bozich | 435/96 |
| 4,977,252 | 12/1990 | Chiu | 536/102 |
| 4,985,082 | 1/1991 | Whistler | 127/33 |
| 5,110,612 | 5/1992 | Quarles et al. | 426/548 |
| 5,445,950 | 8/1995 | Kobayashi et al. | 435/99 |
| 5,565,509 | 10/1996 | Nguyen et al. | 524/47 |

FOREIGN PATENT DOCUMENTS

| | | | |
|---|---|---|---|
| 231729 | 8/1993 | European Pat. Off. | C12P 19/14 |
| 37 31 293 A1 | 4/1980 | Germany | C08B 30/12 |
| 46-14706 | 4/1970 | Japan . | |
| 1406508 | 9/1975 | United Kingdom | C13L 1/08 |

OTHER PUBLICATIONS

Henriksnas et al., "Chain–Length Distribution of Starch Hydrolyzate After α or β–Amylase Action", Biotech. And Bioengineering, vol. XX, pp. 1303–1307 (1978).

*Primary Examiner*—Francisco Prats
*Attorney, Agent, or Firm*—Karen G. Kaiser

[57] ABSTRACT

High solids maltodextrin syrups, some of which are useful as the base for remoistenable adhesives, are prepared by a high solids alpha amylase enzyme conversion process. They are characterized by their high solids content (at least 55 wt. %) and light color. A granular chemically derivatized, optionally converted, starch having a degree of substitution of greater than about 0.01 and less than about 0.5 is used as the starting material. The maltodextrins have a reducing sugar content of about 5–19 dextrose equivalent and a distinct polymodal molecular weight distribution. When a granular highly esterified starch (D.S. of 0.5–1.8) is used as the starting material in the high solids process, the resulting enzyme-converted, esterified maltodextrins are characterized by their improved water dispersibility.

5 Claims, 5 Drawing Sheets

CHEMICALLY DERIVED MALTODEXTRINS

This is a divisional application of Ser. No. 08/643,644, filed May 6, 1996, now issued as U.S. Pat. No. 5,795,397.

BACKGROUND OF THE INVENTION

In its broadest sense, the term "dextrin" covers any starch degradation products, with the exceptions of mono- and oligosaccharides, regardless of how the starches are degraded. All dextrins belong to a large and varied group of D-glucose polymers which can be linear, highly branched, or cyclic. Their complexity creates problems in any classification based on their chemical character. Hence, they are often classified based on how they are prepared.

The hydrolytic procedures used for their preparation fall into four major groups: products obtained by hydrolysis of dispersed starch by the action of liquefying enzymes such as amylases; products obtained by the acid hydrolysis of dispersed starch; Schardinger dextrins formed from dispersed starch by the action of Bacillus macerans transglycosylase; and pyrodextrins produced by the action of heat or heat and acid on dry starch.

Maltodextrins include enzyme- and/or acid-converted dextrins, defined by the Food and Drug Administration (FDA) as non-sweet, nutritive saccharide polymers which consist of D-glucose units linked primarily by alpha-1→4 glucosidic bonds and which have a dextrose equivalent (DE) of less than 20. Corn syrup solids are defined by the FDA as dried glucose syrups in which the reducing sugar content is 20 DE or higher. The degree of hydrolysis strongly affects the functional properties of maltodextrins and corn syrup solids.

Manufacturing processes for preparing maltodextrins include single-stage and dual-stage starch slurry processes using acid and/or enzyme. A solids content of about 18–35% is considered high solids.

A single-stage process combines either acid or enzyme conversion at relatively high temperatures with gelatinization of the starch. The hydrolysis may then be continued in hold tanks until the appropriate DE is reached, at which point the hydrolysis is terminated by either pH adjustment or heat deactivation. The product may then be refined or purified, concentrated and spray-dried.

A dual-stage process involves first a high temperature (usually >105° C.) gelatinization/liquefaction with either acid or enzyme to a low DE (usually <3) followed by a high temperature treatment (as in a jet cooker) to ensure gelatinization of the starch. After pH adjustment and lowering of the temperature to around 82°–105° C., a second conversion step, usually with a bacterial alpha-amylase, is conducted until the desired DE is achieved. The enzyme is then deactivated and the product may then be refined and spray-dried.

Some of the patents covering acid- and/or enzyme-conversion of starches to maltodextrins are discussed below.

U.S. Pat. No. 2,609,326 (issued Sep. 2, 1952 to W. W. Pigman et al.) discloses rapidly gelatinizing and dispersing starch granules in hot water while subjecting the starch to intense agitation and shearing, immediately converting the gelatinized and dispersed starch at an elevated temperature with a starch-liquefying amylase characterized by its ability to hydrolyze the starch molecules into large fragments, inactivating the enzyme, and immediately drying the enzyme converted starch. The dry cold water dispersible converted starches are characterized by a very low content of reducing sugars (3% or less).

U.S. Pat. No. 3,560,343 (issued Feb. 2, 1971 to F. C. Armbruster et al.) discloses a process where a starch is acid hydrolyzed to a D.E. less than 15 and then converted with a bacterial alpha-amylase to a DE between 10 and 25.

Japanese 46-14706 (published Apr. 20, 1971) discloses a continuous process for preparing a granular converted starch which swells, but does not dissolve in cold water, and which is reduced in viscosity. A starch alpha amylase mixture having a water content of 40–60%, containing buffer to adjust the pH to 5–7, is cured for several hours at room temperature, or a temperature at or below the gelatinization temperature, after which it is put into a starch dryer maintained at 70°–150° C. During the drying, the temperature and water content change to those suitable for hydrolyzing the starch. The hydrolysis, drying of the hydrolyzed starch, and deactivation of the residual enzyme simultaneously occur during the heating at 70°–150° C. A liquefaction-type amylase shows the strongest hydrolytic activity at 70°–90° C., but at higher temperatures (i.e., above 90° C.), if the moisture content is above 35%, the starch undergoes the hydrolytic activity but is gelatinized at the same time and if the water content of the mixture is less than 30%, it becomes more difficult to gelatinize the starch, but at the same time the hydrolysis by the enzyme shows a tendency to fall off rapidly. To satisfy these opposing tendencies, it is necessary to reduce the water content of the mixture from 40–60% to 30–35% in the dryer and to increase the temperature to 90°–100° C. during the enzyme hydrolysis.

U.S. Pat. No. 3,849,194 (issued Nov. 19, 1974 to F. C. Armbruster) discloses treating a waxy starch with a bacterial alpha-amylase at a temperature above 85° C. to liquify the waxy starch, cooling the liquified waxy starch to about 80° C., and converting the liquified waxy starch with the bacterial alpha-amylase to a D.E. of from about 5 to about 25.

U.S. Pat. No. 3,663,369 (issued May 16, 1972 to A. L. Morehouse et al.) discloses a two-stage hydrolysis. The first stage is carried out with acids or enzymes at elevated temperatures for short periods to liquify the starch with very little dextrinization or saccharification. The second stage is carried out at an alkaline pH with bacterial alpha-amylase to achieve the desired D.E.

U.S. Pat. No. 3,853,706 (issued Dec. 10, 1974 to F. C. Armbruster) discloses hydrolyzing starch with a bacterial alpha-amylase to a D.E. of less than 15, terminating the hydrolysis by heat treatment, and further converting to a DE of between about 5 and 20.

U.S. Pat. No. 3,974,034 (issued Aug. 10, 1976 to H. E. Horn) discloses maltodextrins which are prepared by the enzymatic hydrolysis of an oxidized starch. The starch is first simultaneously liquefied and oxidized at elevated temperatures and then converted with a bacterial alpha amylase to a D.E. not substantially above 20.

U.S. Pat. No. 4,014,743 (issued Mar. 29, 1977 to W. C. Black) discloses a method for the continuous enzyme liquefication of starch. Preferably, the starch is a raw starch, but pregelatinized or modified starches may be used (see Column 6, lines 1–7). A suitable enzyme is bacterial alpha amylase. An enzyme-containing suspension of raw starch (10–45 wt. % on a dry solids basis) is continuously added to an agitated body of heated (77°–99° C.–170°–210° F.) converted starch. The incoming starch is gelatinized and mixed with the partially converted starch to maintain a blend having a viscosity low enough to be readily agitated and pumped. A stream of the blend is continuously removed from the conversion tank and treated to inactivate the enzyme. The process is controlled to limit the maximum viscosity of the blend to a Brookfield viscosity of not over 5000 cps (100 rpm and 88° C.–190° F.). The reducing sugar content is usually less than 3% on a dextrose equivalent basis. A blend of starches that have been subjected to different degrees of enzyme conversion is obtained since the heating and enzyme treatment is not uniform for the individual starch granules or molecules.

U.K. 1,406,508 (published Sep. 17, 1975) discloses a continuous process for liquefying natural or chemically modified starch to give starch pastes having a solid content of up to 70% by weight. The starch in granular form, without the intermediate formation of a slurry, is continuously supplied to a reaction zone where it is subjected to the action of an enzyme (e.g., alpha amylase) in a stirred aqueous medium at an elevated temperature (50°–98° C.) and pH of 4.5–8. Once the liquefaction is completed the liquefied starch is stabilized by deactivating the enzyme. A greater proportion of large molecules and a broader molecular weight distribution results as compared to a discontinuous process where the molecules are smaller and substantially the same size.

DE 37 31 293 A1 (laid open Apr. 8, 1980) discloses a process for continuously degrading and digesting starch. A dry starch powder together with liquid water or an aqueous starch suspension is charged to a stirred converter containing a starch degrading enzyme, preferably alpha amylase, while the temperature is increased to 70°–90° C. by the injection of steam at 120°–125° C. and 2–4 bar. The product leaving the converter is treated with an enzyme deactivating agent before final dilution to the desired concentration.

U.S. Pat. No. 4,921,795 (issued May 1, 1990) to F. A. Bozich, Jr.) discloses an improved slurry method for producing dextrin adhesives using alpha amylase in combination with glucoamylase. The function of the glucoamylase is to eliminate the limit dextrin problem and the mechanical shearing step. The alpha amylase randomly cleaves the α(1→4) linkages of the linear amylose molecules and cleaves the branched amylopectin molecules up to the (1→6) glucosidic linkages of the limit dextrin. The slurry is stirred sufficiently to create a vortex in the aqueous reaction slurry, thereby maintaining adequate mixing without shearing. The hydrolysis is allowed to continue until an optimal mix of fragment sizes is achieved (as indicated by a Brookfield viscosity of 1000–2000 cps at 20 rpm, 110° F., 45–55% solids, and 0 to 16% sodium borate pentahydrate). The enzyme is then inactivated. The Theological properties of the resultant slurry can be adjusted as needed.

There is a need for high solids, stabilized (i.e., chemically derivatized) maltodextrins which can be used where pyrodextrins or maltodextrins are conventionally used, for example in remoistenable adhesives.

SUMMARY OF THE INVENTION

The present invention is directed to a clear, off-white to beige maltodextrin syrup having a solids content of at least 55% by weight, which is prepared from a chemically derivatized converted or non-converted granular starch. The maltodextrin has (i) substituents in an amount sufficient to provide a degree of substitution greater than about 0.01 and less than about 0.5, preferably between 0.05 and about 0.17; (ii) a reducing sugar content of between about 5 and about 19 dextrose equivalents, preferably between about 10 and about 17; and (iii) a polymodal molecular weight distribution having one peak between about 630 to about 1600 Daltons and at least one other peak between about 1600 and about 2,500,000 daltons, preferably peak(s) between about 1600 and about 160,000 daltons.

The chemically derivatized maltodextrin may be prepared from any cereal, tuber, root, legume, or fruit starch.

Typical substituents include ester and/or ether groups and cationic groups such as diethylaminoethyl chloride hydrochloride or 3-chloro-2-hydroxypropyl trimethyl ammonium chloride groups. Suitable ether groups include hydroxyethyl, hydroxypropyl, or like hydroxyalkyl groups. Suitable ester groups include acetate, propionate, butyrate, hexanoate, benzoate, and octenylsuccinate groups and mixed starch esters such as acetate/propionate, acetate/butyrate and the like. Slightly crosslinked starches which contain monofunctional ether and/or ester substituents are also useful herein and can be converted by the process described below.

The high solids maltodextrin syrups are prepared by a high solids enzyme conversion process which comprises the steps of:

a) adding, to chemically derivatized starch having a degree of substitution of about 0.01 to about 0.50, an alpha amylase enzyme and water in an amount sufficient to produce a single phase powdered mixture without a visible free water phase;

b) activating the enzyme by heating the powdered mixture to about the optimum temperature for the enzyme while maintaining a substantially constant moisture content (i.e., ±5% of the starting moisture content) in the mixture;

c) allowing the enzyme to hydrolyze the starch to a degree sufficient to give a chemically derivatized maltodextrin syrup having a reducing sugar content of between about 5 and about 19, preferably between about 10 and about 17; and d) preferably inactivating the alpha amylase after the desired dextrose equivalent is reached.

In step (d) the solids content may be reduced by adding water.

Optionally, the water can be removed from the aqueous maltodextrin syrup and the maltodextrin recovered as a powdered chemically derivatized maltodextrin.

The present invention is also directed to enzyme-converted, highly esterified starch esters having a degree of substitution of about 0.5 to about 1.8 which is characterized by its self emulsifying properties in water. Preferably the starch ester is highly acetylated waxy maize or corn starch ester having a degree of substitution (D.S.) of about 1 to about 1.25. The starch esters are prepared by adding, to a cold water-insoluble starch ester having a degree of substitution of about 0.5 to about 1.8, an alpha amylase enzyme and water in an amount sufficient to produce a powdered mixture without a visible free water phase and allowing the alpha amylase to hydrolyze and liquefy the starch. The alpha amylase may be mixed with a beta amylase or a glucoamylase.

A method for preparing starch esters is described in U.S. Pat. No. 5,321,132 (issued Jun. 14, 1994 to R. L. Billmers et al.), the disclosure of which is incorporated herein by reference. The starch esters have the formula

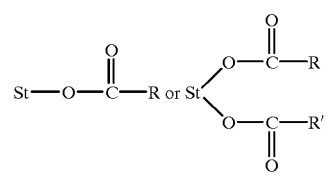

where St is the starch base and R and R' are different and are selected from the group consisting of alkyl, aryl, alkenyl, alkaryl, and aralkyl groups having 1 to 7 carbon atoms. Starch esters of this type include the acetate, propionate, butyrate, hexanoate, benzoate, and mixed esters such as the acetate/propionate. The granular base starch may be any of the native starches described hereafter or may be any of the chemically and/or physically modified starches disclosed in the '132 patent.

The esters are prepared by reacting a granular starch with a sufficient amount of an organic anhydride to obtain the desired D.S. Typically, from about 35–300%, preferably 50–200%, by weight, of anhydride is used based on the dry weight of the starch. The reaction is carried in an aqueous medium at a pH of about 7–11, preferably 7.5–10, and a temperature of about 0°–40° C., preferably 5°–20° C. Because of the high amount of anhydride required, it is desirable to use a concentrated amount of aqueous alkali, e.g., about 10–50%, preferable 20–30%, by weight. Any alkali is suitable. Preferred alkalies are the alkali metal hydroxides, most preferably sodium hydroxide.

As will be shown in the examples, when a starch ester, e.g., the acetate, is converted by the high solids, single phase enzyme conversion process, the original non-water-dispersible starch ester becomes readily dispersible in water at room temperature after the enzyme conversion. The significant reduction in viscosity indicates that the highly substituted starch is hydrolyzed even though chemical substituents typically interfere with enzyme conversion. The hydrolyzed starch still retains a high degree of substitution. The GPC molecular weight profile shows multiple peaks.

As used herein, "starch" is intended to include non-pregelatinized granular starches, pregelatinized granular starches, and starches which are pregelatinized but not cold-water-soluble.

As used herein, "single phase" means a mixture which has no visible free water, whereas a "slurry" consists of two phases, i.e., a water phase and a starch phase. The preferred total water content herein is about 15 to 40% by weight of the total mixture, except when a converted granular starch is being prepared with only alpha amylase where the total water content is about 15–35%.

The powdered or preferably liquid enzyme and sufficient water to give the desired total moisture content are dispersed onto a granular starch powder. The typical moisture content of granular starches is about 10–14%. Thus, sufficient water is added in step (a) to bring the total amount of water to the desired amount. As used herein, the term "total amount of water" refers to the total of the equilibrium moisture typically present in a granular starch and the added water.

If the moist single phase powdered mixture is subjected to a mixing process which kneads and compacts, such as that typical of dough mixing equipment or viscous polymer compounding equipment, it may, depending upon the water content and amount of solubles present, become a very high viscosity compact doughy mass before the onset of gelatinization and conversion. Continued mechanical shearing will raise the temperature and cause gelatinization and conversion.

When the powdered mixture starch contains a granular starch, as the powdered mixture is heated, the heat and moisture initiate the swelling of the starch granules and the starch is completely or partially gelatinized and simultaneously converted. When the powdered mixture contains a pregelatinized, non-cold-water-dispersible starch, the heat and moisture disperse the starch and the starch is fully gelatinized and simultaneously converted. As the starch is converted, usually the powder liquefies. The peak viscosity of the native starch is never reached.

The maltodextrin may be in the form of a syrup, a converted granular starch, or a mixture of the syrup and the converted granular starch. As used herein, "syrup" covers liquids and viscous pastes. The resulting starch syrup is obtained at a high solids content (e.g., at least 60%, typically 65–75% by weight). The syrup may be spray dried, belt-dried, or freeze dried. The enzyme-converted starch may be recovered from the starch syrup as a water-soluble powder. If desired, the sugar by-products may be removed from the granular converted starch by washing.

Optionally, an enzyme activator such as certain inorganic salts and/or a pH adjuster such as an acid, a base, or a buffer may be used.

The enzyme may be activated by direct or indirect heating and/or pH adjustment to the optimum temperature and pH for the particular enzyme used. The enzyme may be inactivated by reducing the pH, adding an inhibiting salt, or increasing the temperature.

The water content during the conversion is affected by the product solids, the condensation of injected steam used for direct heating, and evaporation during the conversion. The product solids are increased by the hydrolysis. During conversion to a D.E. of 100, the dry weight of the starch is increased by 11.11% due to water covalently bound to the hydrolysis reaction products. This dry weight increase is proportional to the degree of conversion. The solids are decreased due to the condensed steam and increased by evaporation.

The powdered mixture of the starch, water, and enzyme does not require stirring during the enzyme conversion step. In contrast to prior art enzyme conversion processes, the process is carried out at such a high solids content that the mixture is a single phase.

Suitable starches can be derived from any source. Typical sources for the starches are cereals, tubers, roots, legumes, fruit starches, and hybrid starches. Suitable native sources include corn, pea, potato, sweet potato, sorghum, wheat, rice, waxy maize, waxy tapioca, waxy rice, waxy barley, waxy wheat, waxy potato, waxy sorghum, and the like.

Using the unique high solids, single phase enzyme conversion process, one obtains a high solids maltodextrin syrup directly.

DESCRIPTION OF THE PREFERRED EMBODIMENTS

Figure 1:
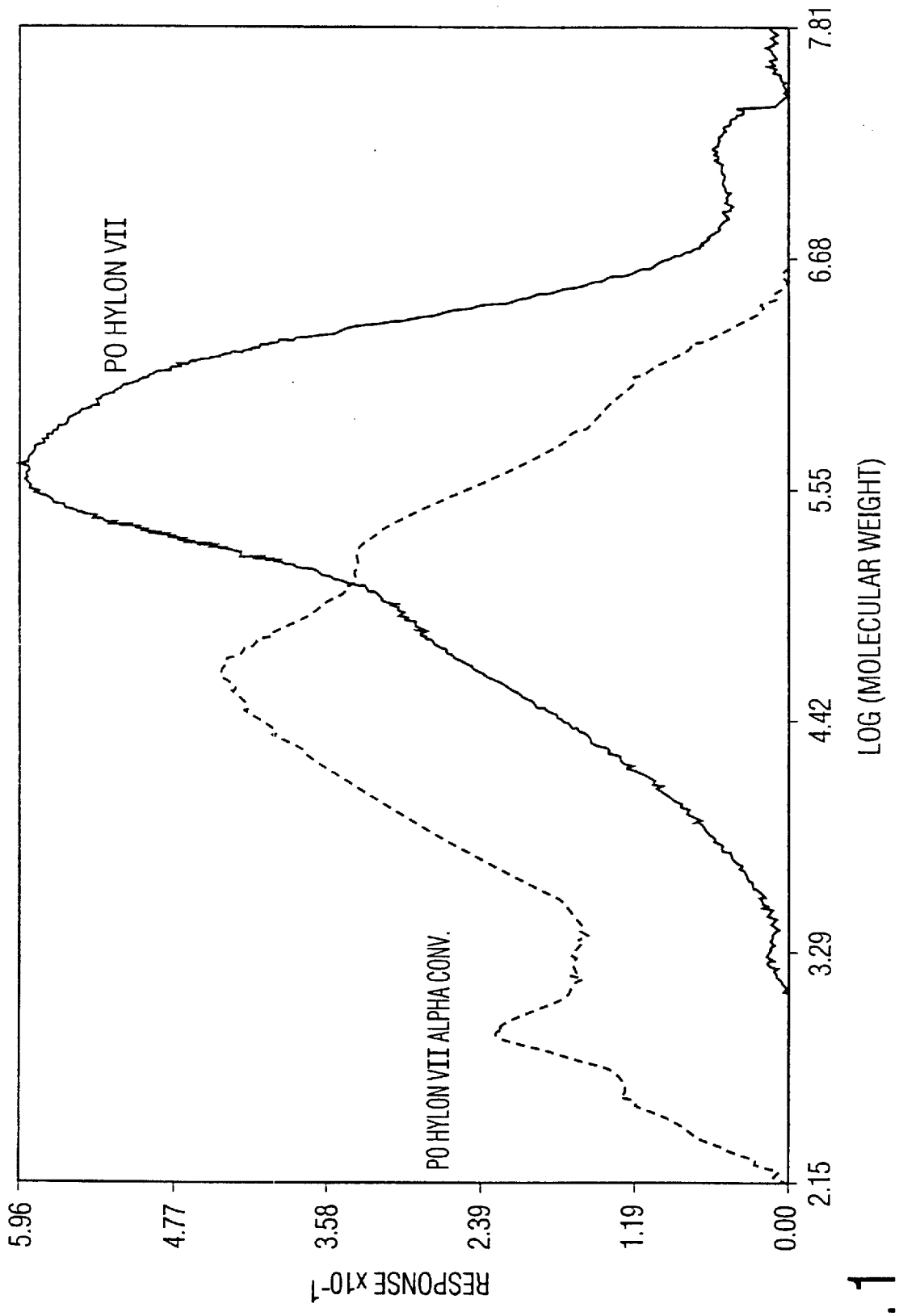
FIG. 1 shows the molecular weight distributions of a non-converted hydroxypropylated high amylose starch (Hylon VII) and an alpha amylase-converted high amylose starch (PO Hylon VII).

There are other potential routes for preparing similar chemically derivatized maltodextrins. For example, a chemically derivatized starch could be slurried in water, cooked to gelatinize and disperse the starch, then enzyme converted with alpha amylase to yield a maltodextrin syrup. There are several drawbacks to this process. First, the solids during the conversion will be limited by the viscosity of either the slurry or the dispersed, unconverted starch, whichever is higher. Second, enzyme activity at lower solids, probably 25 to 40%, will be less than at higher solids and, hence, to obtain comparable enzyme conversion to a D.E. in the maltodextrin range will require high enzyme levels and repeated doses at long conversion times. The claimed products are at or near the limit of conversion for chemically derivatized starches having the desired degree of substitution. This difficult process will only yield similar products at lower solids. Another potential process would be to slurry a native starch in water and then cook and enzyme convert as for conventional, commercial maltodextrins. A commercial maltodextrin having the desired DE and molecular distribution could then be chemically modified. This process, while producing a high solids syrup, has other drawbacks. The by-products of the chemical reaction, i.e., salts such as buffers, pH adjustments by-products, residual reagents, and reagent by-products, will be present in the final syrup limiting the syrup's use in food or products having indirect food contact such as envelope or packaging adhesives. Also, the distribution of the chemical substituents over the range of molecular weight components in the maltodextrin will be different. Further, the chemical derivatization of the maltodextrin tends to produce dark colored products under alkaline conditions. Hydroxypropylated maltodextrins made by this process are black.

Any starch is useful herein. Suitable starches include corn, pea, potato, sweet potato, sorghum, waxy maize, waxy tapioca, waxy rice, waxy barley, waxy potato, and waxy sorghum, and starches having amylose contents of 40% or above (also referred to as high amylose starches). Preferred starches are waxy maize and corn.

It may be possible to convert chemically derivatized flours provided effective enzyme levels are used to obtain the required conversion.

It may be possible to use enzyme-converted, chemically derivatized maltodextrins prepared from starches having an amylose content above 40% (commonly referred to as high amylose starches) which are prepared by the high solids, single phase enzyme conversion process. In order to use these maltodextrins, one would have to use them at lower solids and the adhesives will need to be formulated with additional polyvinyl acetate and humectants to reduce the adhesive's initial viscosity. Further, additional ingredients such as glyoxal, alkalies, or salts will be required to provide the adhesive with long term viscosity stability. The use of humectants causes hygroscopic blocking. The use of salts such as nitrites, ureas, or chlorides causes hygroscopic blocking.

Since high amylose starches are harder to gelatinize, it will also be necessary to use a higher level of chemical substitution to lower the starch's gelatinization temperature. The increased substitution, however, inhibits the enzyme conversion.

Granular starches which have not been pregelatinized are preferred. Granular pregelatinized starches are also useful herein. The pregelatinized granular starches are prepared by processes known in the art. The pregelatinization is carried out in such a way that a majority of the starch granules are swollen, but remain intact. Exemplary processes for preparing pregelatinized granular starches are disclosed in U.S. Pat. Nos. 4,280,851, 4,465,702, 5,037,929, and U.S. Pat. No. 5,149,799, the disclosures of which are incorporated by reference. Predispersed (i.e., pregelatinized starches) can also be used in the high solids, single phase enzyme conversion process provided they are not cold-water-soluble. They can be prepared by jet-cooking and spray-drying.

Chemically derivatizing the starch can lower the gelatinization temperature and make it easier to carry out the conversion. The chemical modifications useful herein include heat- and/or acid-conversion, oxidation, phosphorylation, etherification, esterification, and conventional enzyme modification. These modifications are preferably performed before the starch is enzyme converted. Procedures for chemically modifying starches are described in the chapter "Starch and Its Modification" by M. W. Rutenberg, pages 22–26 to 22–47, Handbook of Water Soluble Gums and Resins, R. L. Davidson, Editor (McGraw-Hill, Inc., New York, N.Y. 1980).

Physically modified starches, such as the thermally-inhibited starches described in WO 95/04082 (published Feb. 9, 1995), are also suitable for use herein provided they have also been chemically modified.

Suitable enzymes for use herein include bacterial, fungal, plant, and animal enzymes such as endo-alpha-amylases which cleave the 1→4 glucosidic linkages of starch, beta-amylases which remove maltose units in a stepwise fashion from the non-reducing ends of the alpha-1,4-linkages, glucoamylases which remove glucose units in a stepwise manner from the non-reducing end of starch molecules and cleave both the 1→4 and 1→6 linkages and mixture of the enzymes with debranching enzymes such as isoamylase and pullulanese which cleave the 1→6 glucosidic linkages of amylopectin-containing starches. Alpha amylases or mixtures thereof with other enzymes are preferred and are used for preparing the enzyme-converted chemically derivatized maltodextrins having unique bimodal or polymodal molecular weight profiles.

Enzymes can be purified by selective absorption or precipitation, but many commercial products contain significant amounts of impurities in the form of other enzymes, as well as in the form of inert protein. For example, commercial bacterial "amylases" will sometimes also contain "proteinases" (enzymes which break down protein). After extraction and partial purification, commercial enzymes are sold either as powders or as liquid concentrates.

Process conditions for the use of a particular enzyme will vary and will usually be suggested by the supplier. The variables include temperature, pH, substrate solids concentration, enzyme dose, reaction time, and the presence of activators. Very often there are no absolute optimum reaction conditions. The "optimum" pH may depend on temperature; the "optimum" temperature may depend on reaction time; the "optimum" reaction time may depend on cost, and so on. The reaction time can vary from 10 minutes to 24 hours or more, typically 1 to 4 hours for alpha amylase. The recommended conditions therefore are usually compromises.

The stability of an enzyme to adverse conditions is usually improved by the presence of its substrate. Some enzymes are also stabilized by certain salts (bacterial amylase is stabilized by calcium salts). It is necessary rigorously to exclude heavy metals and other enzyme poisons, such as oxidizing agents, from an enzyme reaction. These materials usually result in permanent inactivation (i.e., denaturization) of the enzyme. There are many instances however where enzyme activity is reduced reversibly, frequently by the products of a reaction (product inhibition) or by a substance which is structurally related to the usual substrate (competitive inhibition). Reversible inhibitors complex temporarily with the enzyme and therefore reduce the amount of enzyme available for the normal reaction.

Typical enzyme reaction conditions are discussed in "Technology of Corn Wet Milling" by P. H. Blanchard, Industrial Chemistry Library, Vol. 4 (Elsevier, New York, N.Y. 1992).

Test Procedures

Dextrose Equivalent

A Fehling Volumetric Method, as adapted from the Eynon-Lane Volumetric Method #423 of the Cane Sugar Handbook by Spencer and Mead (John Wiley and Son Inc.), is used to determine the D.E.

A starch solution (w/v) of known concentration on an anhydrous starch basis is prepared. The usual concentration is 10 g/200 ml. The starch solution is transferred to a 50 ml/burette. To 50 ml of distilled water in a 500 ml Erlenmeyer flask are added by pipette 5 ml each of Fehling Solutions A and B. Fehling Solution A contains 34.6 g of copper sulfate ($CuSO_4 \cdot 5H_2O$) dissolved in and brought to volume in a 500 ml volumetric flask. Fehling Solution B contains 173 g of Rochelle salt ($NaKC_4H_4O_6 \cdot 4H_2O$) and 50 g of sodium hydroxide dissolved in and brought to volume in a 500 ml volumetric flask. The Fehling Solutions are standardized against Standardized Dextrose obtained from the Bureau of Standards.

To determine the Fehling Factor, the test procedure is followed except that 0.5000 anhydrous grams of dextrose per 200 cc of distilled water is used as the test solution. Using the following formula the factor is then computed:

$$\text{Factor} = \frac{100 \times \text{cc used in titration} \times \text{g dextrose/cc}}{100}$$

The factor applies to both Fehling solutions A and B and is computed to 4 decimal places. The contents of the flask are brought to a boil over a hot plate. The starch solution, while at a boil, is titrated to the distinctive reddish-brown colored end point (precipitated cuprous oxide complex). The ml of starch solution used is recorded.

The contents of the flask are brought to a boil over a hot plate. The starch solution, while at a boil, is titrated to the distinctive reddish-brown colored end point (precipitated cuprous oxide complex). The ml. of starch solution required recorded.

The D.E. is calculated as follows:

$$\% \text{ DE} = \frac{(\text{Fehling Factor}) \times 100}{(\text{g/ml starch concentration} \times \text{ml starch solution})}$$

were the starch solution ("starch sol.") equals the ml of starch solution used in the titration to reach the end point and starch concentration ("starch concn.") equals the concentration of the starch solution on an anhydrous basis expressed in g/ml.

Gel Permeation Chromatography (GPC)

Molecular weight (MW) distribution is determined using a Water Associates GPC-150C Model with a refractive index (RI) detector. Two PL gel columns ($10^5$ and $10^3$ obtained from Polymer Laboratories of Amherst, Ma.) made of highly crosslinked spherical polystyrene/divinylbenzene, are connected in sequence. Dextrans from American Polymer Standards Corp. (Mentor, Ohio) are used as the standards. The experimental conditions are a column temperature of 80° C. and a flow rate of 1 ml/min. The mobile phase is dimethyl sulfoxide (DMS) with 5 mM of sodium nitrate ($NaNO_3$). The sample concentration is 0.1%. The injection volume is 150 μl.

Brookfield Viscometer

Test samples are measured using a Model RVT Brookfield Viscometer and the appropriate spindle which is selected based on the anticipated viscosity of the material. The test sample is placed in position and the spindle is lowered into the sample to the appropriate height. The viscometer is turned on and the spindle is rotated at a constant speed (e.g., 10 or 20 rpm) for at least 3 revolutions before a reading is taken. Using the appropriate conversion factors, the viscosity (in centipoises) of the sample is recorded.

EXAMPLES

In the examples which follow, non-pregelatinized granular starches are used unless it is otherwise stated and the various enzymes described hereafter were used.

The alpha amylases were Ban 120 L and Termamyl. They were obtained from Novo Nordisk. Ban 120 L is a conventional alpha amylase with an optimum temperature of approximately 70° C., optimum pH of 6.0–6.5, an activity of 120 KNU/g, and recommended usage (based on the weight of the starch) of 0.005–1.0, preferably 0.01–0.5. Termamyl is a heat-stable alpha amylase with an optimum temperature greater than 90° C., an activity of 120 KNU/g, and recommended usage (based on the weight of the starch) of 0.005–1.0, preferably 0.01–0.5. One Kilo Novo unit (1 KNU) is the amount of enzyme which breaks down 5.26 g of starch (Merck, Amylum Solubile, Erg. B6, Batch 994 7275) per hour in Novo Nordisk's standard. Method for determining alpha amylase using soluble starch as the substrate, 0.0043M calcium content in solvent, 7–20 minutes at 37°C. and pH 5.6.

EXAMPLE 1

This example shows the conversion of a chemically derivatized high amylose starch (70% amylose) using the high solids, single phase enzyme conversion process.

A hydroxypropylated high amylose starch (PO Hylon VII—D.S. 0.47) (1000 g) was placed in a Ross Mixer with standard blades (Charles Ross & Son Co., Hauppauge, N.Y.). Sufficient water was added to give a total water content of 40%; 0.2% Termamyl was used. The starch was hydrolyzed at 98° C. for 4 hours, the starch was liquefied, and upon cooling the final product was a viscous solution.

FIG. 1 shows the molecular weight distribution of the hydroxypropylated Hylon VII and the alpha amylase converted hydroxypropylated Hylon VII.

EXAMPLE 2

This example shows the conversion of a waxy maize starch ester using the single phase, high solids enzyme conversion process.

An octenylsuccinic anhydride (OSA) treated waxy maize was treated with a mixture of alpha-amylase and beta-amylase as described in Example 1, using 1,000 g of starch, 40% total water, and a mixture of 1.0 g of Ban 120 L and 0.5 g of Spezyme. The mixture was held at 60° C. for 4 hours.

A doughy material was formed. The product was broken up and air-dried. Part of the product (400 g) was slurried in 1,000 ml of water, adjusted to pH 3.0 for 30 minutes with 0.1M hydrochloric acid, adjusted back to pH 6.0 with 3% sodium hydroxide, and spray-dried.

Figure 2:
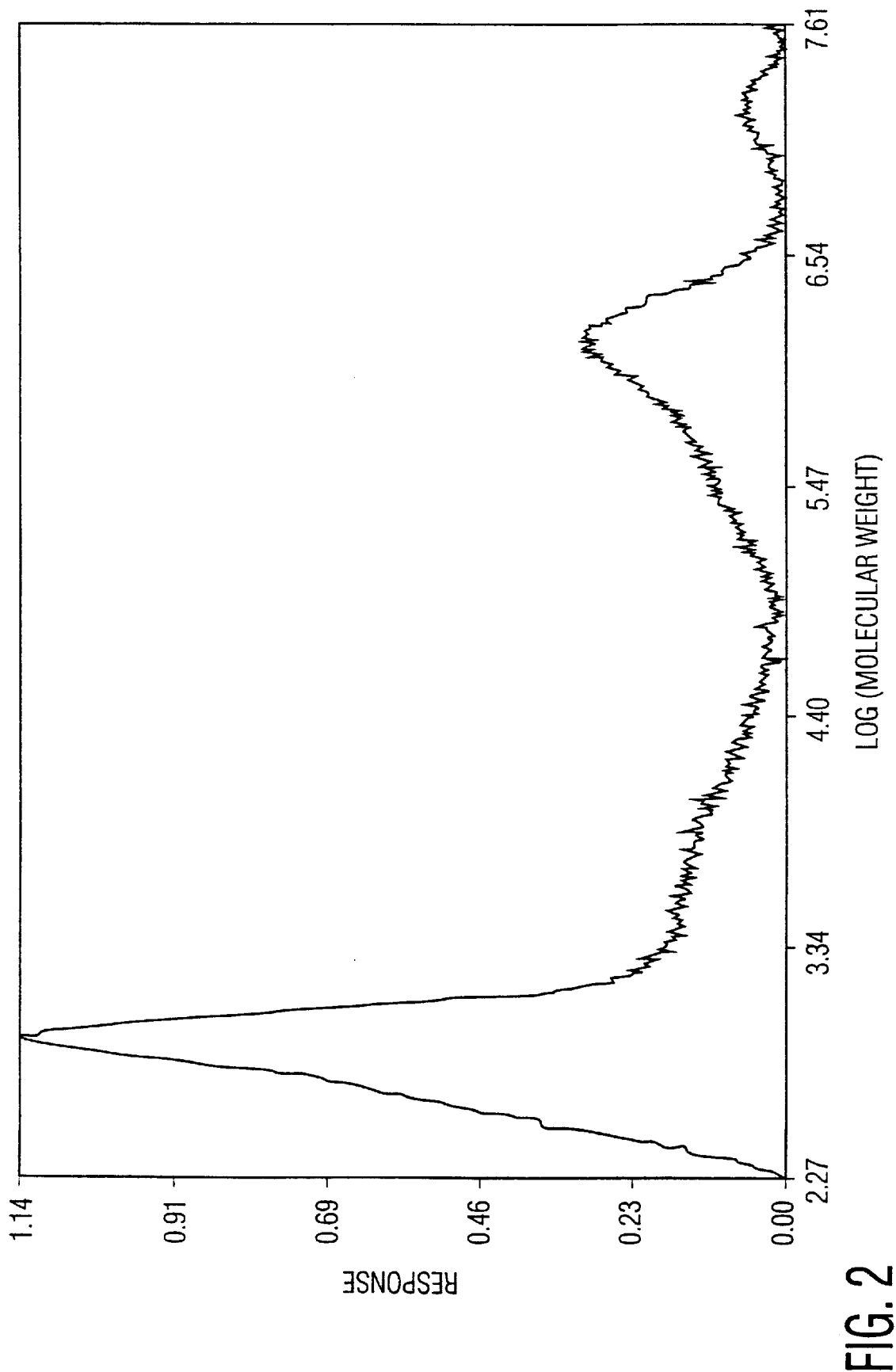
FIG. 2 shows the molecular weight distribution of a waxy maize octenylsuccinate enzyme converted using a mixture of alpha amylase and beta amylase.

The results show that when the OSA-treated waxy maize was converted with a mixture of alpha-amylase and beta-amylase, a low molecular weight peak (800) was observed (see FIG. 2). However, the low normalized area of the peaks detected indicates that most of the sample is excluded and not detected. The low molecular weight-material was estimated to be about 12% based on the weight of the final product.

EXAMPLE 3

This example describes a series of enzyme conversions run in a ten gallon gate mixer reactor using Ban (B) and Termamyl (T), and mixtures thereof. The resulting maltodextrins were used in remoistenable adhesives.

Part A

Preparation of Enzyme-Converted Chemically Derivatized Maltodextrins

The internal dimensions of the tank were 16 inches tall by 16 inches diameter. The gate agitator, made from ½ inch wide by 2 inch deep stainless steel bar stock, had four vertical rakes 10½ inches tall. The outside rakes cleared the inside tank wall by ½ inch; the inside rakes were 3¼ inches from the outside set. Attached to the tank top were four breaker bars, of the same bar stock, located 1¼ and 5¼ inches in from the tank wall. A electric drive, variable from 0 to 60 rpm, powered the agitator. A vent in the tank top provided variable draft forced exhaust. The tank sides and bottom were jacketed for steam heating or water, cooling. A ½ inch diameter steam injection port was provided in the side wall 1 inch above the tank bottom. A thermocouple probe was attached to the bottom of one outside breaker bar. In the tank bottom a 2 inch port with a ball valve was provided for product draw off. For these conversions a removable metal plug was inserted into the draw port, flush with the tank bottom, to eliminate the possibility of a portion of the initial dry charge receiving non-uniform moisture, enzyme, or heat.

For each conversion 33 pounds of a commercially dry granular starch was added to the tank. The enzyme charge was diluted with sufficient water to bring the charge to 25 percent moisture on an anhydrous basis. This water/enzyme mix was added to the starch with mixing. The mixture, after addition of the enzyme/water mix, was a blend of dry starch and moist starch aggregates less the one half inch in diameter.

At this point, the agitator is turned off for about 30 minutes to allow the water to diffuse through out the starch. The starch, after this rest, was a moist flowable powder.

The mixture was heated, generally by injection of live steam (at 32 psi except where indicated otherwise) into the mixture and/or optionally by heating the tank jacket. Typically, the mass was mixed during heating, but this was not required. Mixing only improved heat transfer.

As the granular starch gelatinized (or the cold-water-insoluble predispersed starch was solubilized), it was converted and the reaction mixture changed from a moist powder to a wet doughy mass and then to a dispersed syrup. These changes occurred as the temperature was increased from 50° C. to 90° C. The temperature at which the onset of liquefaction occurred varied depending on the water activity, enzyme activation temperature, and starch type.

In this vented tank, there was some loss of moisture during the full heating cycle. When the injection steam was shut off, the temperature was maintained at the indicated temperature with jacket heating for 30 minutes. The batch was then cooled to less than 50° C. and drawn off. Optionally, the pH was reduced to 3.5 with phosphoric and the mixture was held for 30 minutes to deactivate any residual enzyme. The pH was readjusted if required.

To 43.52 parts of the indicated starch were added a mixture of 6.95 parts water and the indicated amount of Ban 120 L and/or Termamyl. A gate mixer was at 30 rpm while the premix was slowly added in steady stream. Mixing was continued until the starch was uniformly damp. The agitator was shut down and the mixture was heated with live steam and jacketed steam to 82°–93° C. (180°–200° F.) for 30 minutes. Then 6.94 parts of water were added.

The mixer was restarted and agitation was continued at 30 rpm while the mixture was being heated at 93°–99° C. (200°–210° F.). When the adhesive product clarified and was smooth, the viscosity and solids were tested. After the test results were recorded, the pH was adjusted to 3.5 with 85% phosphoric acid, and additional acid added, if needed, to end the enzyme activity.

Figure 3:
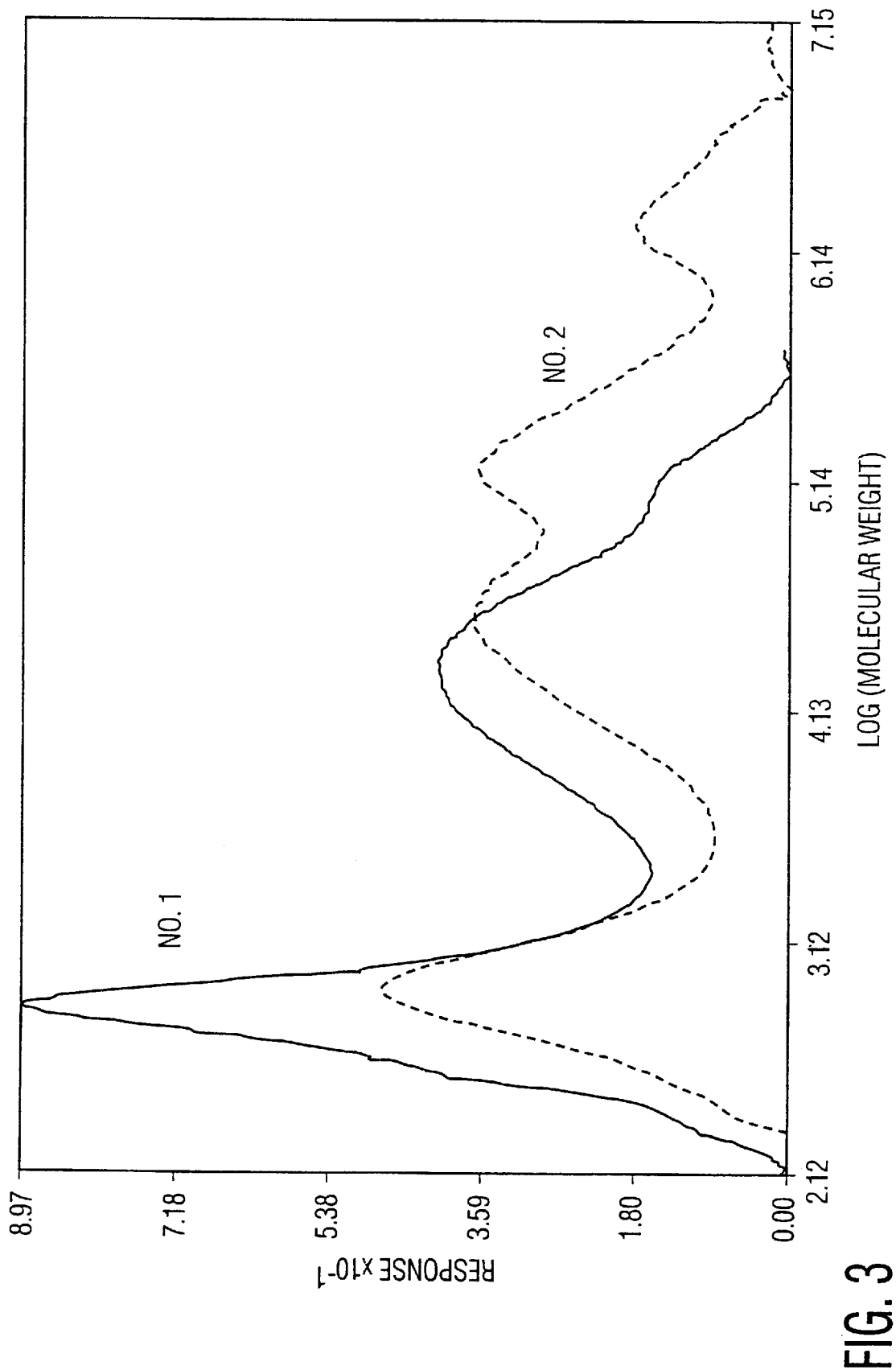
FIG. 3 shows the molecular weight distributions of fluidity hydroxypropylated waxy maize starches enzyme converted with a mixture of alpha amylases (Sample No. 1) and a heat stable alpha amylase (Sample No. 2).
Figure 4:
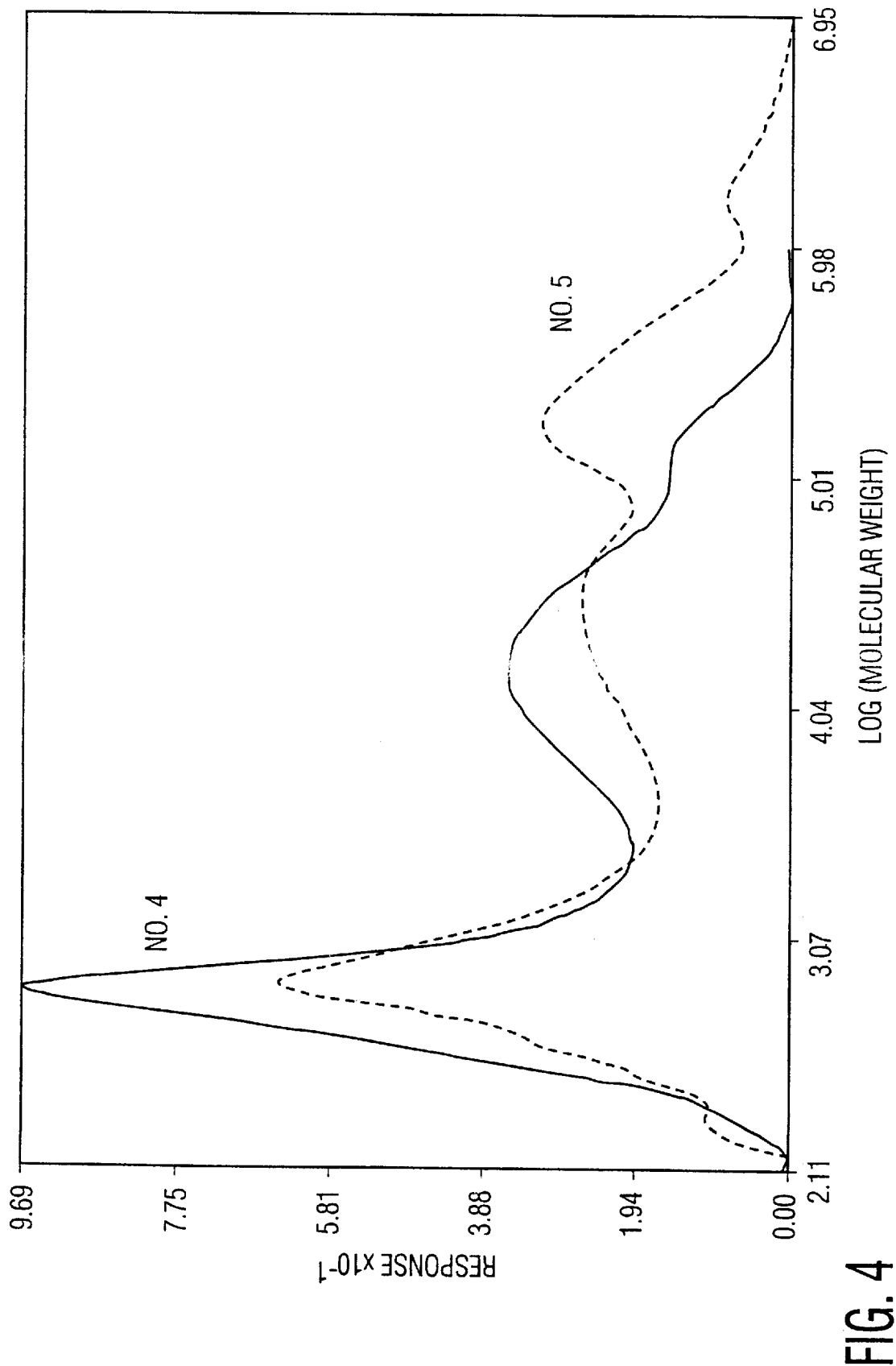
FIG. 4 shows the molecular weight distributions of an alpha amylase-converted waxy maize (Sample No. 4) and an alpha amylase-converted waxy maize octenylsuccinate (Sample No. 5).

The starch base used, enzyme and amount used, and properties of the resulting suitable and comparative maltodextrins (solids, D.E., and D.S.) are summarized in Table 1. The three month viscosity stability of the same maltodextrins is reported in Table 2. The GPC molecular weight profiles of Sample Nos. 1 and 2 are shown in FIG. 3 and of Sample Nos. 4 and 5 are shown in FIG. 4.

TABLE 1

| No. | Starch | Enzyme | Maltodextrin Solids | D.E. | D.S. |
|---|---|---|---|---|---|
| 1* | 35 WF, Hydroxypropylated Waxy Maize | 0.045 B 0.045 T | 62.2 | 13.7 | 0.16 |
| 2 | 35 WF, Hydroxypropylated Waxy Maize | 0.09 T | 70.9 | 11.0 | 0.16 |
| 3 | 35 WF, Hydroxypropylated Waxy Maize | 0.18 T | 62.8 | 10.6 | 0.16 |
| 4 | Hydroxypropylated Waxy Maize | 0.09 T | 68.9 | 13.2 | 0.09 |
| 5 | Octenyl-succinate Waxy Maize | 0.09 T | 60.2 | 15.2 | 0.02 |
| 6** | 35 WF, Hydroxypropylated Waxy Maize | 0.045 T 0.045 T | 60.0 | 7.4 | 0.16 |
| 7 | 35 WF, Hydroxypropylated Waxy Maize | 0.09 T | 69.0 | | 0.16 |

*For Sample No. 1, the steam pressure was 8 psi.
**For Sample No. 6, the enzyme addition was carried out in two steps.

EXAMPLE 4

This example shows the preparation of an enzyme-converted, highly acetylated starch which is characterized by its water dispersibility. It was prepared using the single phase, high solids process.

Part A

Waxy maize was acetylated using the procedure of U.S. Pat. No. 5,321,132, discussed previously. The starch solids were 40% (as is), the pH 8.5, the temperature 25° C., and reaction time 4 hours. The granular starches (1.05 D.S.) were recovered by filtering, washing to less than 500 micromhos conductivity, and air dried to 10% moisture.

Part B

The water-insoluble acetylated waxy maize starch (1.05 D.S.) was converted by alpha amylase, as described above, using 1,000 g starch, 40% total water, and 1 ml each of Ban 120L and Termamyl. The starch began to liquify at about 80° C. A watery liquid product was observed in the Ross Mixer as the temperature increased to 95°–98° C. After the mixture was held at 95°–98° C. for 2 hours, a hardened, rock-like material formed in the Ross mixer.

Figure 5:
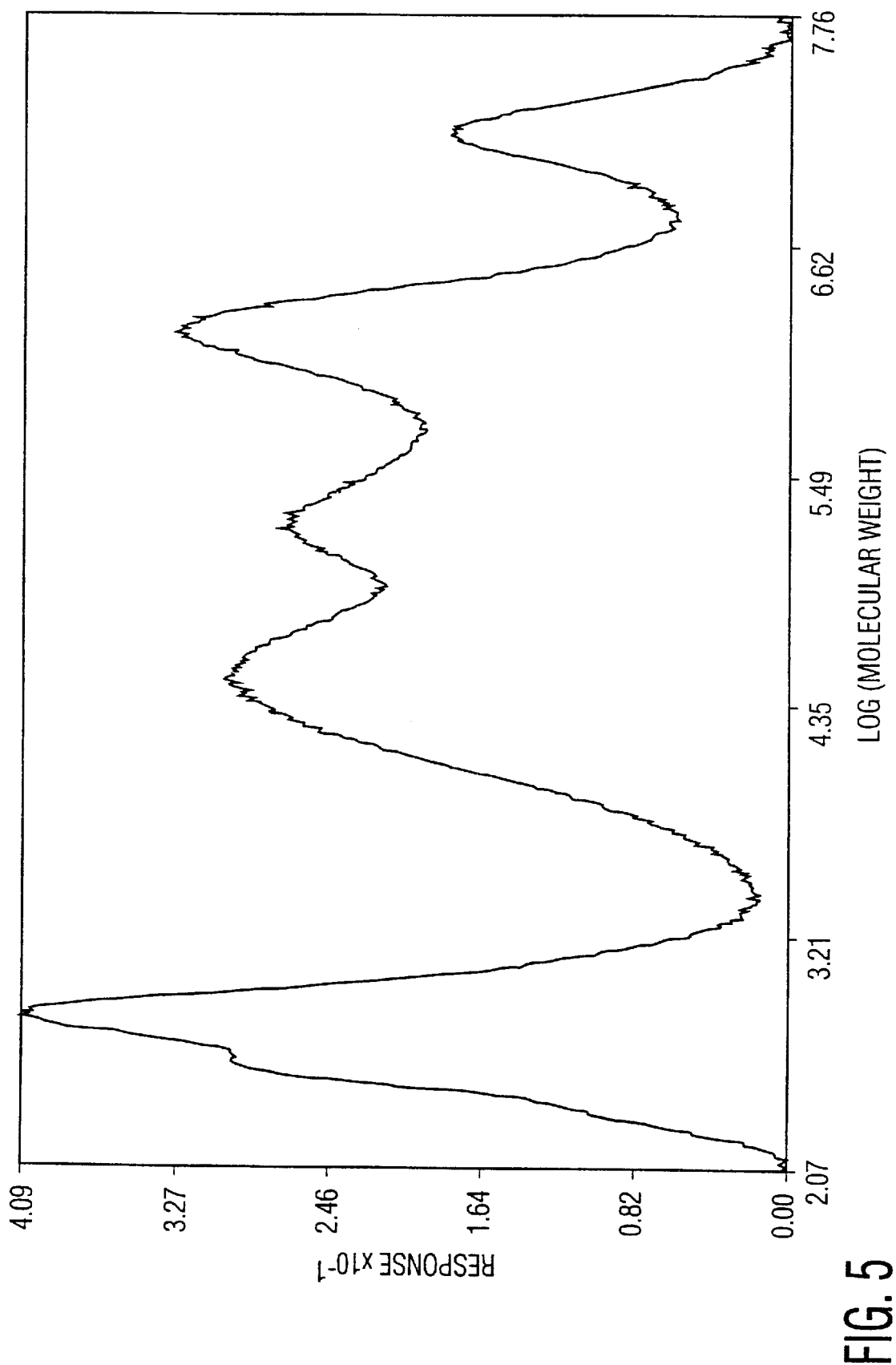
FIG. 5 shows the molecular weight profile of an alpha amylase-converted highly substituted waxy maize starch acetate (D.S. 1.05).

The unconverted acetylated waxy maize (1.05 D.S.) cannot be detected by GPC, probably because of its high molecular weight or great hydrodynamic volume in the DMSO mobile phase. The GPC molecular weight profile of this converted acetylated waxy maize (1.05 D.S.) showed multiple peaks (see FIG. 5). Its Brookfield viscosity (5% solids in DMSO, Spindle #1, 100 rpm) was 56 cps, whereas the Brookfield viscosity of the non-converted acetylated waxy maize at the same concentration was 2,480 cps (5 solids, Spindle #4, 20 rpm). This significant viscosity reduction indicates that the acetylated waxy maize has been hydrolyzed and depolymerized even though it had a D.S. of 1.05.

Part C

A 3.4 gram sample of the above enzyme-converted intermediate D.S. acetylated waxy maize was dispersed in 96 grams of distilled water at room temperature with mixing provided by a magnetic stirrer. Within a few minutes, the sample had dispersed into a milky white dispersion. A small portion settled out over several hours. The remaining dispersion was stable for three days at room temperature. The dispersed cloudy product turned into a clear solution when propanol or ethanol was added. The high alcohol solubility indicates that the enzyme-converted product still contains a high degree of acetate substitution.

This demonstrates the utility of the enzyme converted, intermediate D.S. acetylated waxy maize prepared by the high solids, single phase process in application areas where the converted starch will be added as an aqueous emulsion.

Now that the preferred embodiments of the invention have been described in detail, various modifications and improvements thereon will become readily apparent to those skilled in the art. Accordingly, the spirit and scope of the present invention are to be limited only by the appended claims and not by the following specification.

What is claimed is:

1. An enzyme-converted, highly esterified starch ester having a degree of substitution of about 1.0 to about 1.8, wherein the starch is first esterified and then subsequently converted.

2. The starch ester of claim 1 characterized by its water dispersibility, wherein the starch is acetylated waxy maize or corn starch ester.

3. The starch ester of claim 1, wherein the degree of substitution is about 1 to about 1.25.

4. The starch ester of claim 1 which is prepared by the steps of:

(a) adding, to a cold water-insoluble starch ester having a degree of substitution of about 0.5 to about 1.8, an alpha amylase enzyme and water in an amount sufficient to produce a single phase powdered mixture without a visible free water phase;

(b) activating the alpha amylase by heating the mixture to the optimum temperature for the alpha amylase; and (c) allowing the alpha amylase to hydrolyze the starch ester.

5. The ester of claim 4, wherein the starch is a non-pregelatinized granular waxy maize starch or corn starch and wherein the alpha amylase is mixed with a beta amylase or a glucoamylase.

* * * * *